(12) United States Patent
Dahlhauser

(10) Patent No.: US 6,610,486 B1
(45) Date of Patent: *Aug. 26, 2003

(54) METHODS OF SCREENING NUCLEIC ACIDS FOR NUCLEOTIDE VARIATIONS

(75) Inventor: Paul A. Dahlhauser, Nashville, TN (US)

(73) Assignee: Genetic Assays, Inc., Nashville, TN (US)

(*) Notice: Subject to any disclaimer, the term of this patent is extended or adjusted under 35 U.S.C. 154(b) by 104 days.

This patent is subject to a terminal disclaimer.

(21) Appl. No.: 09/717,793

(22) Filed: Nov. 20, 2000

Related U.S. Application Data

(63) Continuation-in-part of application No. 09/137,075, filed on Aug. 20, 1998, now Pat. No. 6,150,105.

(51) Int. Cl.⁷ .......................... C12Q 1/68; C12P 19/34; C07H 21/02

(52) U.S. Cl. ......................... 435/6; 435/91.2; 435/94; 435/194; 435/325; 435/419; 536/23.1; 536/24.3

(58) Field of Search .................... 435/6, 91.2, 94, 435/194, 325, 419; 536/24.3, 233

(56) References Cited

U.S. PATENT DOCUMENTS

| | | | |
|---|---|---|---|
| 5,202,231 A | 4/1993 | Drmanac et al. | 435/6 |
| 5,354,656 A | 10/1994 | Sorge et al. | 435/6 |
| 5,698,400 A | 12/1997 | Cotton et al. | 435/6 |
| 5,710,028 A | 1/1998 | Eyal et al. | 435/91.1 |
| 5,736,373 A * | 4/1998 | Hamilton | 435/194 |
| 5,744,306 A * | 4/1998 | Murtagh, Jr. et al. | |
| 6,150,105 A * | 11/2000 | Dahlhauser | 435/6 |

FOREIGN PATENT DOCUMENTS

| | | | |
|---|---|---|---|
| EP | 0 412 883 | 2/1991 | C12Q/1/68 |
| WO | WO 95/00669 | 1/1995 | C12Q/1/68 |
| WO | WO 96/30545 | 10/1996 | C12Q/1/68 |
| WO | WO 97/35033 | 9/1997 | C12Q/1/68 |

OTHER PUBLICATIONS

Bi and Stambrook "Detection of known mutation by proof-reading PCR", *Nucleic Acids Research*, 26(12):3073–3075 (1998).

Brow, et al. "Differentiation of Bacterial 16S rRNA Genes and Intergenic Regions and *Mycobacterium tuberculosis katG* Genes by Structure–Specific Endonuclease Cleavage", *Journal of Clinical Microbiology*, 34(12):3129–3137 (Dec. 1996).

Cotton, et al. "Reactivity of cytosine and thymine in single-base–pair mismatches with hydroxylamine and osmium tetroxide and its application to the study of mutations", *Proc. Natl. Acad. Sci. USA*, 85:4397–4401. (Jun. 1988).

Chee, et al. "Accessing Genetic Information with HighDensity DNA Arrays", *Science* 274:610–614 (Oct. 25, 1996).

Higgins, et al. "Competitive Oligonucleotide single–Base Extension Combined with Mass Spectrometric Detection for Mutation Screening", *BioTechniques* 23:710–714 (Oct. 1997).

Hovig, et al. "Constant denaturant gel electrophoresis, a modification of denaturing gradient gel electrophoresis, in mutation detection", *Mutation Research* 262:63–71 (1991).

Labeit, et al. "Laboratory Methods—A New Method of DNA Sequencing Using Deoxynucleoside α–Thiotriphosphates", *DNA* 5(2):173–177 (1986).

Liu, et al. "Bi–directional dideoxy fingerprinting (Bi–ddF): a rapid method for quantitative detection of mutations in genomic regions of 300–600 bp", *Human Molecular Genetics* 5(1):107–114 (1996).

Liu, et al. "Restriction Endonuclease Fingerprinting (REF): A Sensitive Method for Screening Mutations in Long, Contiguous Segments of DNA", *BioTechniques* 18(3):470–477 (1995).

Lipshutz, et al. "Using Oligonucleotide Probe Arrays To Access Genetic Diversity", *BioTechniques* 19(3):442–447 (1995).

Lu, et al. "Detection of Single DNA Base Mutations with Mismatch Repair Enzymes", *Genomics* 14:249–255 (1992).

Myers, et al. "Detection of Single Base Substitutions by Ribonuclease Cleavage at Mismatches in RNA:DNA Duplexes", *Science* 230:1242–1246 (1985).

Nagamine, et al. "A PCR Artifact: Generation of Heteroduplexes", *Am. J. Hum. Genet.* 45:337–339 (1989).

(List continued on next page.)

*Primary Examiner*—Jeffrey Fredman
(74) *Attorney, Agent, or Firm*—Needle & Rosenberg, P.C.

(57) ABSTRACT

The present invention provides a method of detecting nucleotide variation within a first nucleic acid, comprising generating a set of single-stranded extension products from a first nucleic acid in the presence of modified nucleotide bases, wherein the extension products incorporate modified nucleotides and thereby limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of selected labeled nucleotides, wherein extension products that terminate with a 3'-nucleotide that does not hybridize with the corresponding position on the reference nucleic acid are replaced with one or more nucleotides that hybridize with the corresponding nucleotides on the reference nucleic acid and wherein those extension products that had a non-hybridizing nucleotide at the 3'-terminus can now be distinguished from those extension products that had a hybridizing nucleotide at the 3'-terminus, and distinguishing those extension products that had a non-hybridizing nucleotide at their 3'-terminus from those extension products that had a hybridizing nucleotide at their 3'-terminus, thereby detecting nucleotide variation in the first nucleic acid. Alternatives of this method are also provided which can also detect mutations in a nucleic acid at the penultimate 3'-terminal position on the single-stranded extension products.

52 Claims, 5 Drawing Sheets

OTHER PUBLICATIONS

Newton, et al. "Analysis of any point mutation in DNA. The amplification refractory mutation system (ARMS)", *Nucleic Acids Res.* 17(7):2503–2516 (1989).

Novack, et al. "Detection of single base–pair mismatches in DNA by chemical modification followed by electrophoresis in 15% polyacrylamide gel", *Proc. Natl. Acad. Sci. USA* 83:586–590 (Feb. 1986).

Orita, et al. "Rapid and Sensitive Detection of Point Mutations and DNA Polymorphisms Using the Polymerase Chain Reaction", *Genomics* 5:874–879 (1989).

Pastinen, et al. "Multiplex, fluorescent, solid–phase minisequencing for efficient screening of DNA sequence variation", *Clinical Chemistry* 42(9):1391–1397 (1996).

Porter, et al. "Direct PCR sequencing with boronated nucleotides", *Nucleic Acids Research* 25(8):1611–1617 (1997).

Rosenbaum, et al. "Temperature–gradient gel electrophoresis. Thermodynamic analysis of nucleic acids and proteins in purified form and in cellular extracts", *Biophysical Chemistry* 26:235–246 (1987).

Sarkar, et al. "Dideoxy Fingerprinting (ddF): A Rapid and Efficient Screen for the Presence of Mutations", *Genomics* 13:441–443 (1992).

Winter, et al. "A method to detect and characterize point mutations in transcribed genes: Amplification and overexpression of the mutant c–Ki–ras allele in human tumor cells", *Proc. Natl. Acad. Sci. USA* 82:7575–7579, (Nov. 1985).

Wu, et al. "Allele–specific enzymatic amplification of β–globin genomic DNA for diagnosis of sickle cell anemia" *Proc. Natl. Acad. Sci. USA* 86:2757–2760 (Apr. 1989).

* cited by examiner

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<221> NAME/KEY: Oligonucleotide, Single-Stranded
<223> OTHER INFORMATION: Amplification Primer

<400> SEQUENCE: 1
cagagaaacc tttatctg                                            18

<210> SEQ ID NO 2
<211> LENGTH: 17
<212> TYPE: DNA
<213> ORGANISM: Artificial Sequence
<220> FEATURE:
<221> NAME/KEY: Oligonucleotide, Single-Stranded
<223> OTHER INFORMATION: Amplification Primer

<400> SEQUENCE: 2
gtactggtgg agtattt                                             17

METHODS OF SCREENING NUCLEIC ACIDS FOR NUCLEOTIDE VARIATIONS

This application is a continuation-in-part of Ser. No. 90/137,075 filed Aug. 20, 1998 now U.S. Pat. No. 6,150,105.

BACKGROUND OF THE INVENTION

1. Field of the Invention

This invention relates to the field of detecting nucleotide variations in a nucleic acid. More particularly, the invention relates to methods of detecting nucleotide variations in a nucleic acid by generating variable length copies of a nucleic acid from a sample, hybridizing those generated nucleic acids to reference nucleic acids, and detecting the presence or absence of nucleotide variations at the 3'-terminal position or the penultimate 3'-position on the variable length nucleic acids.

2. Background Art

The number of diseases that are linked to gene mutations continues to increase as the sequence of the human genome is unraveled. Nucleic acid sequencing is the ultimate standard for detecting nucleotide variations. Nucleic acid sequencing is well suited for detecting unknown mutations or polymorphisms that may occur at any base within a target nucleic acid segment. The chemistry of enzymatic DNA sequencing, the most commonly used method, has essentially remained the same since its conception (Sanger et al., Proc. Natl. Acad. Sci. U.S.A., 74, 5463 (1977)). The art has been improved by technology that has allowed for its automation such as the introduction of fluorescent dyes, robotics and improved electrophoretic systems with automated detection. However, if genetic variations occur at a low frequency in the sample population, automation comes at a cost that is too high for most laboratories. Even in a manual mode, sequencing can be cost prohibitive because it is labor intensive. Thus, there is a need in the art for a simple inexpensive process to screen nucleic acids for unknown nucleotide variations prior to sequencing.

That need in the art is evident by the number of methods being developed to screen for unknown mutations. Single strand conformation polymorphism (SSCP) detects mutations in an unknown sample by comparing its migration rate in a single stranded state to a known sample in a non-denaturing gel, as disclosed by Orita et al., Genomics, 5:874–879 (1989). Changes in nucleotide sequence affect the secondary structure or conformation of a DNA molecule which may alter its migration rate during electrophoresis. This technique, however, is limited to small targets less than 200 bp, has limited sensitivity, and requires rigid electrophoresis conditions to be reproducible. Improvements in SSCP analysis such as dideoxy fingerprinting, both unidirectional (Sarkar et al., Genomics, 13:441–443 (1992)) and bidirectional (Liu et al., Hum. Mol. Genet., 5:107–114 (1996)), and restriction endonuclease fingerprinting (Liu and Sommer, Biotechniques, 18:470–477 (1995)) can detect mutations over a 1 kb span but sacrifice sensitivity for simplicity since the complex pattern of DNA bands generated by these processes makes it difficult to readily detect mutations.

Another method that is used for screening for nucleotide variations in a nucleic acid is based on the differential mobility of heteroduplex molecules as they migrate through a gel matrix. In its simplest form called heteroduplex analysis, an uncharacterized DNA segment, usually an amplification or PCR product, is mixed with the corresponding wild type segment, heated, and allowed to slowly renature, as first described by Nagamine et al. (Am. J. Hum. Genet., 45, 337–339 (1989)). If the uncharacterized nucleic acid has a different sequence than the wild type sequence, heteroduplex molecules are formed. Base mismatches in the heteroduplex alter its migration rate allowing it to be partially resolved from the homoduplex in a non-denaturing gel.

A more sensitive approach called denaturing gradient gel electrophoresis (DGGE) subjects heteroduplex molecules to increasing levels of denaturant in a gradient gel format, as first described by Fisher and Lerman. (Proc. Natl. Acad. Sci. U.S.A., 80:1579–1583 (1983)). As the heteroduplex molecules migrate through the denaturant, they begin to melt, or denature. At this point migration is slowed and is no longer linear. The melting point is slightly different for homoduplex molecules, allowing partial resolution of heteroduplex molecules. Precise control of field strength, temperature and time are critical to achieving reproducible results, and difficult to consistently reproduce.

With constant denaturing gel electrophoresis (CDGE), these variables are less critical since the concentration of denaturant is the same throughout the gel (Hovig et al., Mut. Res., 262:63–71 (1991)). A significant limitation of this technique is that a nucleic acid segment may have more than one melting domain for which separate gels at different denaturant concentrations must be run.

Temporal temperature gradient gel electrophoresis (TTGE) seeks to circumvent this problem by gradually increasing the temperature during electrophoresis, as described by Borresen et al. (Bioradiations, 99:12–113 (1997)). This is a hybrid technique between CDGE and temperature gradient gel electrophoresis which uses temperature only as a denaturant (Rosenbaum and Riesner, Biophys. Chem., 26:235–246 (1987)). As expected, however, this technique is also difficult to perform and also difficult to reproduce.

A recently introduced technique called base excision sequence scanning (BESS) improves upon dideoxy fingerprinting with ddTTP by obviating the need for a separate sequencing reaction (Epicentre Technologies, Madison, Wiss.). The target of interest is amplified by PCR using a labeled primer and a limiting amount of dUTP. After amplification, the products are treated with uracil DNA glycosylase to cleave at uracil sites. Denaturing gel electrophoresis of the fragments then produces a ladder almost identical to a dideoxy T sequencing ladder. The technique is useful for screening DNA segments up to 1 kb for mutations, but is limited by the resolution of gel electrophoresis and it does not detect G to C transversions or vice versa.

Another recently introduced technique uses a structure specific endonuclease called cleavase to digest intrastrand structures and produce fragment length polymorphisms (CFLP) and is described by Brow et al., J. Clin. Microbiol., 34:3129–3137 (1996). The structures are created by denaturing a segment of DNA and then quickly cooling it to the digestion temperature and adding the enzyme. The folding pattern for a given segment may be altered by sequence variations that upon digestion with the enzyme produces a unique banding pattern on a denaturing gel. This technique, however, is severely limited by the resolution of the gel electrophoresis and the complex pattern of DNA bands generated by the process which makes it difficult to detect mutations.

Detection of mutations by chemical or enzymatic cleavage of base pair mismatches in heteroduplex DNA has been described by Noack et al., Proc. Natl. Acad. Sci. U.S.A., 83:586–590 (1986), Cotton et al. Proc. Natl. Acad. Sci. U.S.A., 85:4394–4401 (1988), Cotton et al., U.S. Pat. No. 5,202,231, (Winter et al., Proc. Natl. Acad. Sci. U.S.A., 82:7575–7579 (1989), Myers et al., Science, 230:1245–1246 (1985)), (Lu and Hsu, Genomics, 14:249–255 (1992),) and U.S. Pat. No. 5,698,400. Many of these techniques are limited by the inability of the cleavage reagents to recognize all types of base pair mismatches, and for others this can be overcome by analyzing both strands of a DNA segment. To date, widespread use of these techniques has not been observed, partly because they require highly toxic reagents and the procedures are difficult to perform.

The miniaturization of the DNA hybridization process onto a small solid surface, known as a DNA chip or micro array, allows the analysis of DNA segments without gel electrophoresis. See Macevicz, U.S. Pat. No. 5,002,867, Drmanac., U.S. Pat. No. 5,202,231, Lipshutz et al., Biotechniques, 9(3):442–447 (1995) and Chee et al., Science, 274:610–614 (1996). The resolution of gel electrophoresis, however, strictly limits the size of the DNA segment that can be analyzed for all of the aforementioned mutation detection technologies including DNA sequencing and the high cost of the equipment,and chips used in this process limit its wide spread use.

The present invention provides needed improvements over these prior art methods by providing methods which can detect all possible base variations including single and multiple base substitutions, insertions and deletions. These variations may occur at one or more sites and affect one or more nucleotides at each site for a given locus. Secondly, as a screening process, these methods provide a clear positive or negative result. Thirdly, the process is not limited by the resolution power of gel electrophoresis and therefore allowing the analysis of DNA segments greater that 1 kb in size. Lastly, by way of eliminating electrophoretic detection, it is highly amenable to automation and therefore suitable for high volume screening.

SUMMARY OF THE INVENTION

In accordance with the purpose(s) of this invention, as embodied and broadly described herein, this invention, in one aspect, relates to a method of detecting nucleotide variation within a first nucleic acid, comprising generating a set of single-stranded extension products from a first nucleic acid in the presence of modified nucleotide bases, wherein the extension products incorporate modified nucleotides and thereby limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of selected labeled nucleotides, wherein extension products that terminate with a 3'-nucleotide that does not hybridize with the corresponding position on the reference nucleic acid are replaced with a nucleotide that hybridizes with the corresponding nucleotide on the reference nucleic acid and wherein those extension products that had a non-hybridizing nucleotide at the 3'-terminus can now be distinguished from those extension products that had a hybridizing nucleotide at the 3'-terminus, distinguishing those extension products that had a non-hybridizing nucleotide at their 3'-terminus from those extension products that had a hybridizing nucleotide at their 3'-terminus, thereby detecting nucleotide variation in the first nucleic acid.

The invention also provides a method of detecting within a first nucleic acid the presence of a nucleotide variation, comprising generating a set of single-stranded extension products in the presence of modified nucleotide bases, wherein the extension products incorporate modified nucleotides that limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of a selected modified nucleotide which is resistant to further replacement and when incorporated into an extension product inhibits further extension of the extension product, wherein extension products that terminate with a non-modified nucleotide can be further extended and thereby distinguished from those extension products that cannot be further extended, removing the unincorporated selected modified nucleotide, extending those extension products that can be further extended, distinguishing those extension products that are further extended from those extension products that cannot be further extended, thereby detecting nucleotide variation in the first nucleic acid.

The invention further provides a method of detecting nucleotide variation within a first nucleic acid, comprising generating a set of single-stranded extension products in the presence of modified nucleotide bases and chain-terminating nucleotide bases from a first nucleic acid, wherein the extension products incorporate modified nucleotides that limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended, extending those extension products that can be further extended, distinguishing those extension products that are further extended from those extension products that cannot be further extended, thereby detecting nucleotide variation in the first nucleic acid.

DETAILED DESCRIPTION OF THE INVENTION

Figure 1:
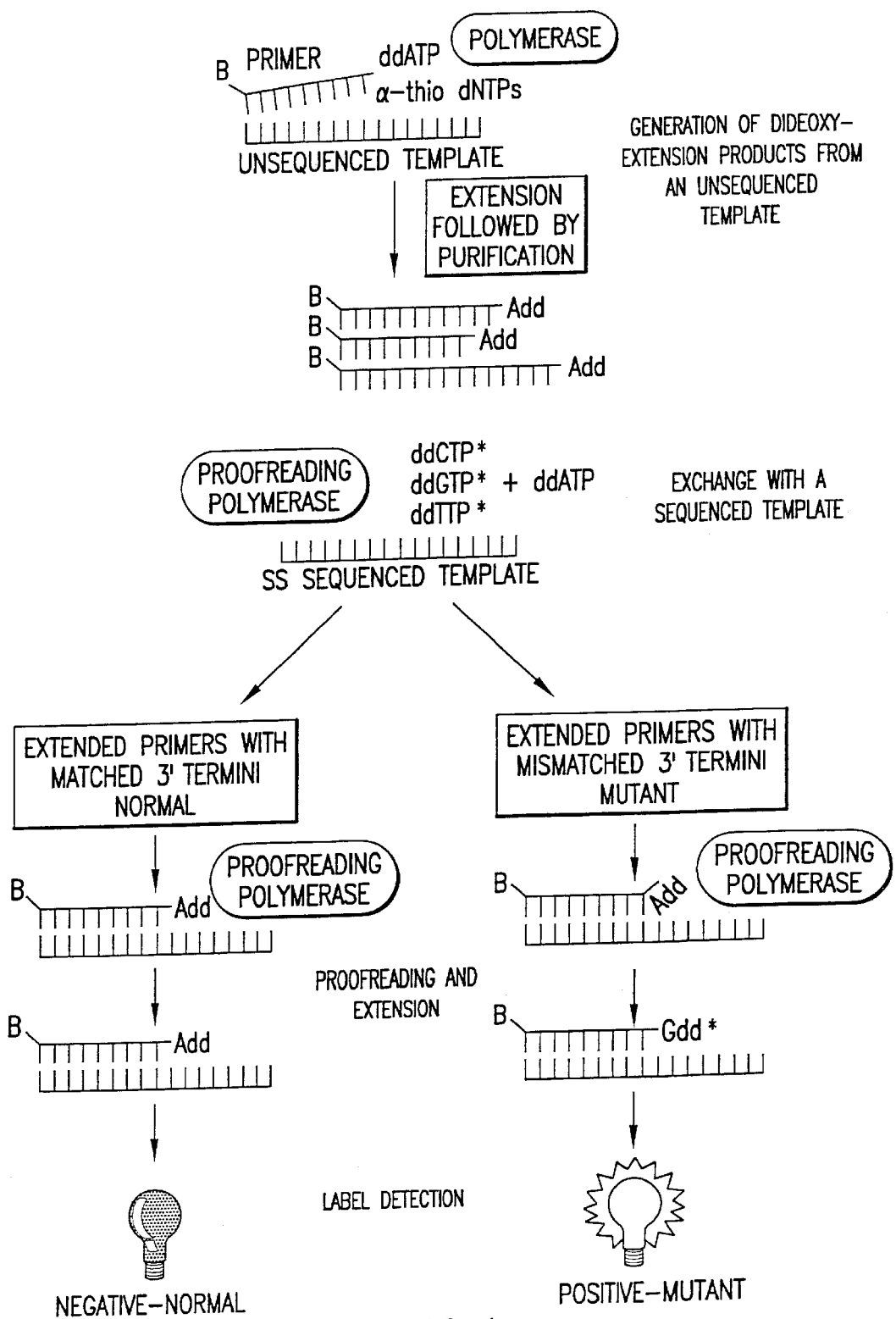
FIG. 1 shows a schematic for the single-base extension template exchange reaction extension detection method.

The present invention may be understood more readily by reference to the following detailed description of the preferred embodiments of the invention and the Examples included therein.

Before the present compounds and methods are disclosed and described, it is to be understood that this invention is not limited to specific nucleic acids, chain terminating nucleotides, editing enzymes, extension and/or amplification enzymes, detectable moieties, and other reagents used in the methods described herein, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reference to "a nucleic acid" includes multiple copies of the nucleic acid and can also include more than one particular species of molecule.

In one aspect, the invention relates to a method of detecting nucleotide variation within a first nucleic acid, comprising generating a set of single-stranded extension products from a first nucleic acid in the presence of modified nucleotide bases, wherein the extension products incorporate modified nucleotides and thereby limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of selected labeled nucleotides, wherein extension products that terminate with a 3'-nucleotide that does not hybridize with the corresponding position on the reference nucleic acid are replaced with a nucleotide that hybridizes with the corresponding nucleotide on the reference nucleic acid and wherein those extension products that had a non-hybridizing nucleotide at the 3'-terminus can now be distinguished from those extension products that had a hybridizing nucleotide at the 3'-terminus, distinguishing those extension products that had a non-hybridizing nucleotide at their 3'-terminus from those extension products that had a hybridizing nucleotide at their 3'-terminus, thereby detecting nucleotide variation in the first nucleic acid.

Nucleotide variation as used herein refers to any nucleotide substitution at one or more positions in a nucleic acid (the first nucleic acid) and any insertion or deletion at one or more positions on a nucleic acid, and any combination thereof. For example, a nucleic acid can have a single base substitution in a region that is being assayed, or that nucleic acid can have multiple base substitutions in the region, or any combination of base substitutions, insertions, and deletions. Nucleotide variation as used herein also refers to any nucleotide modification that could give rise to an altered phenotype or genotype. The methods described herein can detect the presence of a base substitution, a deletion, and an insertion, and any other mutation that causes a nucleotide on a nucleic acid to not hybridize with the corresponding nucleotide on a separate, at least partially complementary nucleic acid.

The first nucleic acid can be a single stranded or double stranded nucleic acid from a sample, i.e. a patient or experimental sample, and the reference nucleic acid can be a standard or reference nucleic acid to which the first nucleic acid is hybridized, and/or compared. In the methods described herein, one or more strands of the first nucleic acid are used to generate a set of single-stranded extension products that are at least partially resistant to 3'→5' exonuclease activity and can optionally contain a chain-terminating nucleotide or deoxynucleotide at their 3'-terminus, to generate a set of single-stranded extension products of variable length.

The generation or isolation of the first nucleic acid for use in the invention can be optionally facilitated by amplification of the target region by cloning the region of interest into a replication vector such as a plasmid or a phage, to generate either double or single stranded molecules. If the first nucleic acid is generated by cloning the nucleic acid, there are many known techniques for isolating the nucleic acid from the cloning vector after the nucleic acid within the cloning vector has been replicated, such as phage isolation, plasmid isolation via lysis of bacteria followed by denaturation of the cellular proteins and centrifugation of the nucleic acids, or even density banding of plasmid or phage nucleic acids by density gradient centrifugation.

One skilled in the art will recognize that there are many other known amplification techniques for generating copies of one or more strands of a nucleic acid, such as the polymerase chain reaction (PCR). Other amplification techniques can also be used to amplify a nucleic acid, however, the self-sustained sequence replication (3SR) system, the transcription-based amplification system (TAS), and the RNA replication system based on Qβ replicase. The product of the amplification, the first nucleic acid, and/or the reference nucleic acid can therefore be a DNA or an RNA, either single stranded or double stranded. If the product of the amplification is double stranded, single strands can be isolated by methods well known in the art, such as the use of biotin-linked amplification primers or the selective degradation of a phosphorylated strand using lambda exonuclease as described by Higuchi and Ochman, *Nucleic Acids Research,* 17:5865 (1989). Alternative methods for the production of single stranded templates are also known in the art such as asymmetric PCR (Ausbel et al., "Current Protocols in Molecular Biology", John Wiley & Sons, New York (1987)) and solid phase capture (Holtman et al., *Nucleic Acids Research,* 17:4937–4946 (1989)). If the product of the amplification procedure is an RNA, DNA can be generated from that RNA using techniques well known in the art such as the use of reverse transcriptase.

Whether the first nucleic acid for use in the methods described herein has been amplified or whether the first nucleic acid is obtained directly, such as from a patient sample or any other experimental sample, that nucleic acid is then used as a template for generating a set of single-stranded extension products of variable length. For example, a chain-terminating dideoxynucleotide can be used in the reaction such that the resultant set of single-stranded extension products contains single-stranded extension products that terminate at each position where the dideoxynucleotide is incorporated. Preferably, the set of variable-length single-stranded extension products in this embodiment would contain at least one single-stranded extension product that incorporated a dideoxynucleotide into every available position for that particular species of dideoxynucleotide; i.e. a "sequencing ladder." Generation of dideoxy sequencing ladders is well known in the art and may be accomplished with commercially available sequencing kits. In a preferred embodiment of the present invention, the sequencing ladder is generated by thermal cycle sequencing to generate a plurality of sequencing ladders corresponding to the first nucleic acid to facilitate later detection of those single-stranded extension products that have 3'-terminal nucleotide that hybridizes to a nucleotide at the corresponding position on a reference nucleic acid or a 3'-terminal nucleotide that does not hybridize to a nucleotide at the corresponding position on a reference nucleic acid.

Alternatively, the set of single-stranded extension products of variable length can be generated by different procedures. For example, the single-stranded extension products can be generated by extension of the primer sequence without chain-terminating nucleotides present in the reaction mixture, but where the deoxynucleotides are present in a limiting amount. Alternatively, the deoxynucleotides can be present in a sufficient amount to synthesize a set of single-stranded extension products that correspond to the total length of the first nucleic acid, but which are then used to generate a set of variable length single-stranded extension products through partial terminal degradation of the single-stranded extension products, for example, using exonuclease I or III, or T4 DNA Polymerase in the absence of or a limiting amount of deoxynucleotides. One skilled in the art will appreciate that the particular technique or techniques used to generate the set of single-stranded extension products can vary.

One skilled in the art will also recognize that the generation of the set of single-stranded extension products will require a primer for the extension reaction to proceed. The primer can be internal, such as hybridization of a 3'-region to the 5'-region of the same molecule, or the primer can be external, such as the use of a synthesized primer that can hybridize to a preferred site or sites on the first nucleic acid.

The first nucleic acid, the single-stranded extension products, and the primer can be modified such as by being linked to another molecule such as biotin, digoxigenin, a hapten, an antibody, an enzyme, or another moiety that can facilitate the isolation and/or detection of the molecules. As discussed in the Example section herein, a primer can be linked to biotin, and the set of single-stranded extension products produced as a result of extension reactions using that modified primer can be isolated from the first nucleic acid and the other components of the extension reaction using streptavidin-coated magnetic beads.

Optionally, the modified first nucleic acid, the single-stranded extension products, and/or the primer can be purified or isolated from a reaction mixture and/or other nucleic acids by binding them to a solid support. For example, a nucleic acid complementary to at least a portion of a primer used in the extension reaction can be linked to a solid support, such as beads used in column chromatography, and after the primer has been extended, that reaction mixture can be heated to denature the extension products away from the first nucleic acid, and that mixture passed through the column under conditions such that the extension products hybridize to a nucleic acid linked to the beads and not to the first nucleic acid, and whereby the extension products ate thereby purified from the first nucleic acid. For example, the primer can comprise the sequence complementary to the first nucleic acid and also have a 5' region comprising a sequence not complementary to the first nucleic acid, such as a poly(C) region. The nucleic acid linked to the beads can then comprise a poly(G) region that can hybridize to the poly(C) region under conditions such that the extension product does not hybridize to the first nucleic acid. One skilled in the art will recognize that there are many other examples of procedures used to separate one strand of an extension reaction from its complementary, or partially complementary strand, and the methods described herein are not limited to any specific isolation, separation, or purification procedure.

Alternatively, a primer used to generate the set of single-stranded extension products can be phosphorylated at the 5' end to allow subsequent degradation of the phosphorylated strand with lambda exonuclease as described by Higuchi and Ochman (*Nucleic Acids Research,* 17:5865 (1989)). Alternative methods for the production of single stranded templates are also known in the art such as asymmetric PCR (Ausbel, et al., "Current Protocols in Molecular Biology", John Wiley & Sons, New York (1987)) and solid phase capture (Holtman et al., *Nucleic Acids Research,* 17:4937–4946 (1989)).

The single-stranded extension products are typically generated in the presence of at least one type of modified nucleotide is used in the generation reaction and thereby incorporated in the single-stranded extension products, such that the single-stranded extension products are at least partially resistant to 3'→5' exonuclease activity. The modified nucleotides main function after incorporation as a nucleotide is to limit subsequent 3'→5' exonuclease activity to the 3' dideoxynucleotide. These modified nucleotides are well known in the art and include, but are not limited to, thio-modified deoxynucleotide triphosphates and borano-modified deoxynucleotide triphosphates (Eckstein and Gish, *Trends in Biochem. Sci.,* 14:97–100 (1989) and Porter *Nucleic Acids Research,* 25:1611–1617 (1997)). Boronated nucleotides have been shown to be more readily integrated in an extension reaction by a thermostable polymerase than are thio-modified dNTPs, and have a greater resistance to nucleases (Porter et al., Nucleic Acids res. 25(8):1611–1617 (1997).

After the set of single-stranded extension products of variable length has been generated, and optionally isolated from the first nucleic acid, the single-stranded extension products are then hybridized to a reference nucleic acid. This reference nucleic acid can be a nucleic acid that is typically considered "wild-type" for a particular gene or portion of a gene including structural and regulatory regions of the gene. For example, the reference nucleic acid can be a nucleic acid that is known to be a locus for mutations in or near a particular gene that when mutated, typically gives rise to an altered phenotype or disease in an individual. Alternatively, the mutations can result in a different phenotype that is considered beneficial, such as a bacterial species now being able to detoxify a toxin. Any mutation is contemplated as being detected by the methods described herein, and the specific identity of the mutation does not limit the applicability of these methods. Additionally, the reference nucleic acid can be isolated, generated, synthesized, or amplified for use in the methods described herein by any methods described in the art since the source of the reference nucleic acid is also not limiting to the present methods.

The precise conditions of the hybridizations will, of course, vary depending on the specific sequence of the reference nucleic acid and the first nucleic acid. The specific conditions are readily obtainable by one skilled in the art, and typical hybridization conditions and optimization conditions are available from a wide variety of source references. For example, Innis et al. ("PCR Protocols: A Guide to Methods and Applications" Academic Press, Inc. 1990) and Erlich, H. A. (PCR Technology, Principles and Applications for DNA Amplification) both disclose standard hybridization conditions for nucleic acid amplification, and Sambrook et al. ("Molecular Cloning, a Laboratory Manual" Cold Spring Harbor Laboratory Press (1989)) set forth general methods for typical nucleic acid hybridizations and optimization procedures for those methods. Optionally, the specific hybridization condition for hybridization between the single-stranded extension products and the reference nucleic acids is such that activity of an enzyme which can remove and replace the 3'-terminal nucleotide of the single-stranded extension product is retained, and typically, highly active and specific.

After the single-stranded extension products have been hybridized to the reference nucleic acids, an enzyme that can remove and replace the 3'-terminal nucleotide of the extension products (i.e. a "proofreading" enzyme) is added to these hybrids. In one embodiment of the present invention, this reaction can take place in the presence of a chain-terminating nucleotide and if the 3'-terminal nucleotide hybridizes to the reference nucleic acid, that 3'-terminal nucleotide will be replaced with a chain-terminating nucleotide of the same identity (FIG. 1). Where the 3'-terminal nucleotide of the extension product does not hybridize to the reference nucleic acid, such as where the 3'-terminal nucleotide of the extension represents a mutation in the first nucleic acid at that particular position, the proofreading enzyme will remove this mismatched base on the extension product and replace it with a base that hybridizes to the reference nucleic acid, and which can be detected.

The specific proofreading enzyme used in the methods described herein is not limited to a DNA polymerase, but includes any enzyme, or combination of enzymes which can remove a 3'-terminal nucleotide and can replace that 3'-terminal nucleotide with another nucleotide of the same or different identity. For example, the proofreading enzyme can be, for example, a thermostable polymerase such as Vent® DNA Polymerase, Deep Vent® DNA Polymerase, E. coli DNA Polymerase I, Klenow Fragment DNA Polymerase I, T4 DNA Polymerase, T7 DNA Polymerase, Ultima® DNA Polymerase, and Pfu® DNA Polymerase. Alternatively, the enzyme that removes the 3'-terminal nucleotide can be an exonuclease such as E. coli exonuclease III or exonuclease I used in combination with a polymerase such as T4 DNA Polymerase, to effectively achieve the same result with an additional step. Alternatively, a non-proofreading polymerase can be used in the methods described herein. The inability of a non-proofreading polymerase to extend a mismatch is well known in the art and is the basis of allele specific PCR and amplification refractory mutation systems (ARMS). See Wu et al., *Proc. Natl Acad. Sci. U.S.A.*, 86:2757–2760 (1989) and Newton et al., *Nucleic Acids Res.*, 17:2503–2516 (1989).

Thus, in one embodiment, the invention provides a method of detecting a nucleotide variation within a first nucleic acid, comprising generating a set of single-stranded extension products from the first nucleic acid in the presence of modified nucleotide bases, wherein the extension products incorporate modified nucleotides and thereby limit exonuclease activity to the 3'-terminal nucleotide base, and wherein the extension products have variable lengths; hybridizing the variable length extension products to a reference nucleic acid; contacting the hybridizing nucleic acids with a first enzyme which can remove the 3'-terminal nucleotide of the extension products, and with a second enzyme which extends those extension products that can be further extended in the presence of selected labeled nucleotides, wherein extension products that terminate with a 3'-nucleotide that does not hybridize with the corresponding position on the reference nucleic acid are replaced with a nucleotide that hybridizes with the corresponding nucleotide on the reference nucleic acid and wherein those extension products that had a non-hybridizing nucleotide at the 3'-terminus can now be distinguished from those extension products that had a hybridizing nucleotide at the 3'-terminus; and distinguishing those extension products that had a non-hybridizing nucleotide at their 3'-terminus from those extension products that had a hybridizing nucleotide at their 3'-terminus, thereby detecting nucleotide variation in the first nucleic acid. The hybridizing nucleic acids may either be contacted sequentially with the first enzyme followed by the second enzyme, or contacted simultaneously with the first enzyme and the second enzyme.

The nucleotide that is incorporated into the extension product that had a 3'-terminal nucleotide that did not hybridize to the reference nucleic acid can comprise a nucleotide that can be detected in the presence of nucleotides that have the same identity as the 3'-terminal nucleotide of the extension products where the 3'-terminal nucleotide initially hybridized to the reference nucleic acid. For example, where the extension reaction is performed in the presence of a chain-terminating nucleotide corresponding to dATP, the excision/replacement reaction where the 3'-terminal nucleotide that does not hybridize to the reference nucleic acid is replaced by a nucleotide that does hybridize to the reference nucleic acid can be performed in the presence of radiolabeled dGTP, dCTP, and dTTP. In this example, where any of the radiolabeled dGTP, dCTP, and dTTP nucleotides are incorporated into the extension product, that product can be detected by the presence of radioactivity. Further, the reaction can contain an internal control, such as a differently labeled nucleotide, such as $^{35}$S-dATP or fluorescent dATP in this example, whereby that label can be incorporated into the single-stranded extension product that has a 3'-nucleotide that hybridized to the corresponding position on the reference nucleic acid, so one can monitor the reaction for activity, especially in the event that few or no mutations are detected, since both those extension products that had a hybridizing nucleotide at their 3'-terminal nucleotide and those that had a non-hybridizing nucleotide at the 3'-terminal nucleotide can be detected, and also distinguished. Alternatively, the label can be only incorporated into the extension product that had a hybridizing nucleotide at its 3'-terminal nucleotide position.

The specific label that one uses to detect the presence of a mutation can, of course, vary. For example, the label can comprise a radiolabel, a fluorescent label, a luminescent label, an antibody linked to a nucleotide that can be subsequently detected, a hapten linked to a nucleotide that can be subsequently detected, or any other nucleotide or modified nucleotide that can be detected either directly or indirectly. Therefore the specific method or methods used to distinguish between the single-stranded extension products that had a 3'-terminal nucleotide that hybridized to the reference nucleic acid and the single-stranded extension products that had a 3'-terminal nucleotide that did not hybridize to the reference nucleic acid will vary depending upon the specific label that is used in the methods described herein. For example, if the labeled nucleotide is a radiolabeled nucleotide, the detection method can comprise scintillation counting or exposing the reaction products to film, which when developed, can distinguish between the labeled nucleic acids and the unlabeled nucleic acids.

Also provided by the present invention is a method of detecting within a first nucleic acid the presence of a nucleotide variation, comprising generating a set of single-stranded extension products from the first nucleic acid in the presence of modified nucleotide bases, wherein the extension products incorporate modified nucleotides that limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of a selected modified nucleotide which is resistant to further replacement and when incorporated into an extension product inhibits further extension of the extension product, wherein extension products that terminate with a non-modified nucleotide can be further extended and thereby distinguished from those extension products that cannot be further extended, removing the unincorporated selected modified nucleotide, extending those extension products that can be further extended, distinguishing those extension products that are further extended from those extension products that cannot be further extended, thereby detecting nucleotide variation in the first nucleic acid.

Figure 2:
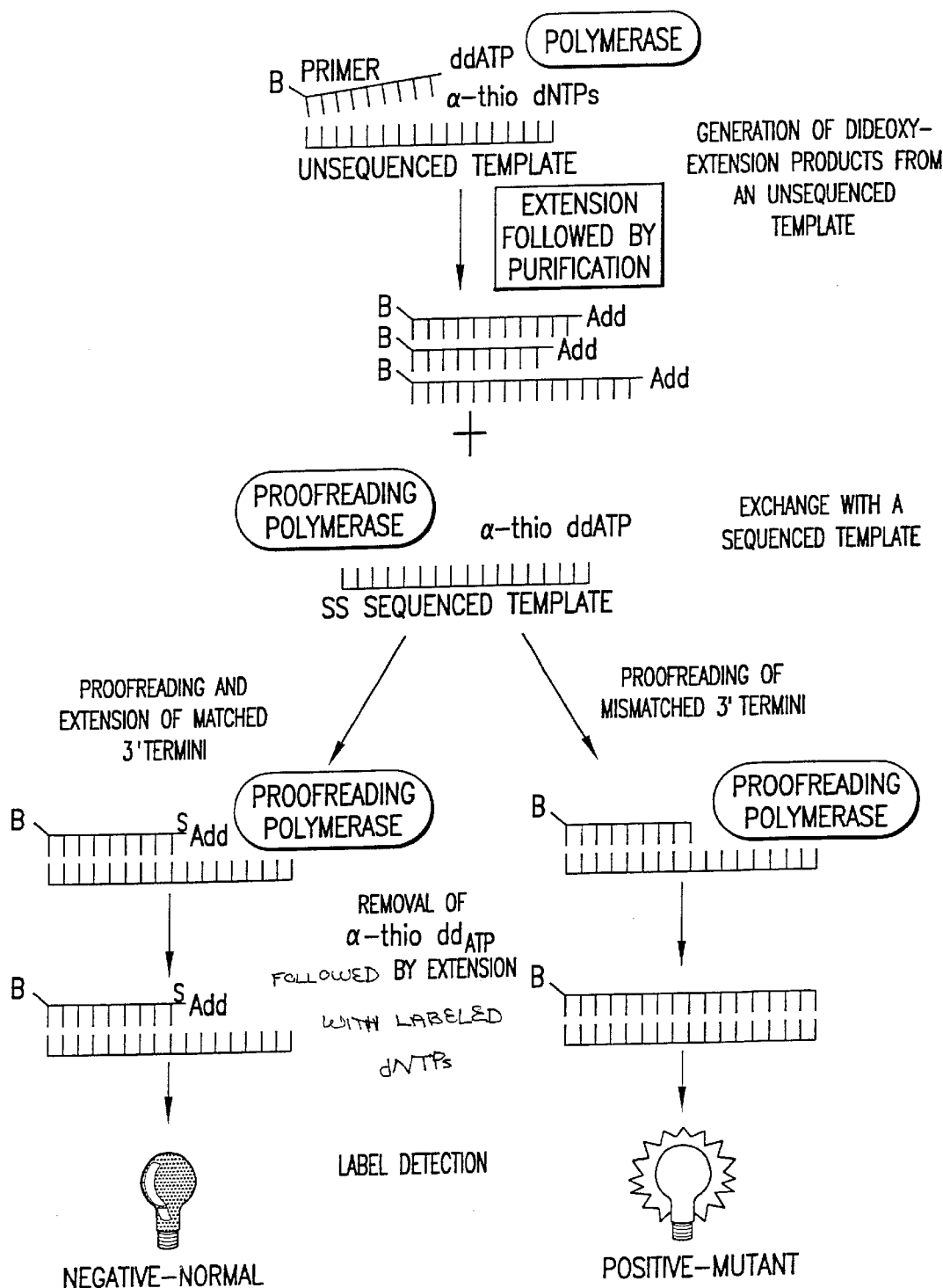
FIG. 2 shows a schematic for the extension detection method.

This particular method is based on the ability of a proofreading polymerase to replace a matching terminal chain-terminating nucleotide such as a dideoxynucleotide with a modified chain-terminating nucleotide that is resistant to 3'→5' exonuclease activity in an irreversible or "suicide" reaction. Single-stranded extension products of variable length generated from a first nucleic acid are mixed with a known template or a reference nucleic acid to form a stable hybrid. The hybrid is exposed to a proofreading polymerase, or in an equivalent reaction thereof as discussed above, in the presence of a chain terminating nucleotide that is resistant to further 3'→5' exonuclease activity, such as a α-thio-dideoxynucleotide, that is the base-equivalent of the 3' base of the extension products, under conditions suitable for excision of the 3'-terminal nucleotide of the extension product and its replacement with the chain terminating nucleotide that is resistant to further 3'→5' exonuclease activity (FIG. 2). If the 3'-terminal nucleotide of the extension product hybridizes to the corresponding position on the first nucleic acid, then that 3'-terminal nucleotide is excised and replaced with a corresponding chain terminating nucleotide that is resistant to further 3'→5' exonuclease activity. The proofreading polymerase enzyme can no longer proofread the 3'-terminal nucleotide and also cannot extend the matching terminal base because it is a chain-terminating nucleotide. If, however, the 3'-terminal nucleotide of the single-stranded extension product does not hybridize to the reference nucleic acid (i.e., there is a mismatch at the terminal base), the proofreading polymerase will excise the 3'-terminal nucleotide of the single-stranded extension product but will not insert a chain-terminating nucleotide into that position, because, for example, a chain-terminating nucleotide which can hybridize to the corresponding position on the reference nucleic acid is not present in the reaction mixture. That proofread extension product can then be further extended and that extended product detected. Thus, extension products whose 3'-terminal nucleotide is complementary to the corresponding position on the reference nucleic acid can be irreversibly terminated whereas extension products whose 3'-terminal nucleotide is not complementary to the corresponding position on the reference nucleic acid can be proofread and ready to serve as primers for a subsequent extension reaction which can be detected.

Thus, in one embodiment, the invention provides a method of detecting within a first nucleic acid the presence of a nucleotide, comprising generating a set of single-stranded extension products from the first nucleic acid in the presence of modified nucleotide bases, wherein the extension products incorporate modified nucleotides that limit exonuclease activity to the 3'-terminal nucleotide base, and wherein the extension products have variable lengths; hybridizing the variable length extension products to a reference nucleic acid; contacting the hybridizing nucleic acids with a first enzyme which can remove the 3'-terminal nucleotide of the extension products, and with a second enzyme which extends those extension products that can be further extended in the presence of a selected modified nucleotide which is resistant to further replacement and when incorporated into an extension product inhibits further extension of the extension product, wherein extension products that terminate with a non-modified nucleotide can be further extended and thereby distinguished from those extension products that cannot be further extended; removing the unincorporated selected modified nucleotide; extending those extension products that can be further extended; and distinguishing those extension products that are further extended from those extension products that cannot be further extended, thereby detecting nucleotide variation in the first nucleic acid. The hybridizing nucleic acids may either be contacted sequentially with the first enzyme followed by the second enzyme, or contacted simultaneously with the first enzyme and the second enzyme.

For a subsequent extension reaction, it may be desirable to remove the chain terminating nucleotide that is resistant to further 3'→5' exonuclease activity from the reaction. This can be accomplished by adding to that reaction mixture an activity that renders the chain terminating nucleotide that is resistant to further 3'→5' exonuclease activity effectively unable to be further added to the single-stranded extension product, such as shrimp alkaline phosphatase which hydrolyzes the triphosphate on the chain terminating nucleotide, after which the enzyme can be thermally inactivated. Alternatively the template and extension products may be purified from the chain terminating nucleotide that is resistant to further 3'→5' exonuclease activity by other methods well known to those ordinary skill in the art, such as molecular weight or size separation, linking the extension products to a solid support as discussed above, and selective degradation of the free nucleotides.

The primer extension reaction in this method may be detected by the incorporation of a label, as discussed above, or indirectly detected, for example, by the release of inorganic pyrophosphate as a result of polymerase mediated nucleoside incorporation during DNA synthesis. (Nyren, *Anal. Biochem.*, 167:235–238 (1987)). This embodiment has an advantage of allowing continuous monitoring of polymerase activity within the reaction. This particular reaction can be initiated by adding nucleoside triphosphate bases, D-luciferin, L-luciferin, ATP sulfurylase, luciferase and an oligonucleotide having the same sequence of a region at or near the 5' end of the known template and that is capable of priming an extension reaction. This oligonucleotide can be used to increase the sensitivity of the assay by reverse priming any full length extension products that are generated, which is particularly important when a mismatch/mutation occurs near the 5' end of the known reference nucleic acid since relatively few nucleotides will be added prior to reaching the end of the template. For typical luminometric detection, see Nyren et al. (*Anal. Biochem.*, 244:367–373 (1997)). The use of a thermostable luciferase will allow the extension reaction to occur at higher temperatures and will increase the sensitivity and specificity of the reaction. (Kaliyama and Nakano, *Biosci. Biotechnol. Biochem.*, 58:1170–1171 (1994)).

Another example of a method for detecting multi-base primer extension utilizes the Fluorogenic 5' Nuclease Assay available from Perkin Elmer, Foster City, Calif. and as described by Holland et al., *Proc. Natl. Acad. Sci. U.S.A.*, 88, 7276–7280 (1991). This method involves labeling a probe, referred to as the TaqMan® probe, with a reporter and quencher dye. The probe can be specific for an internal sequence in the particular nucleic acid being amplified. As Taq DNA polymerase extends the amplification primer it encounters the TaqMan® probe and degrades it with its 5' to 3' exonuclease activity. The dissociation of the reporter from the quencher results in an increase in fluorescence. The application of this method to multi-base extension detection requires only the synthesis of a TaqMan® probe complementary to the 5' terminal sequence of the known template. As with bioluminometric detection, this method allows continuous monitoring of polymerase activity within the reaction. An additional advantage is the high sensitivity and specificity since the reaction can be performed at elevated temperatures in a thermocycling reaction.

In one variation of this method, the step of extending those extension products that can be further extended prior to the detection step can be eliminated where the removal of the unincorporated modified nucleotide can itself comprise a step that can be detected. For example, where the 3'-terminal base is a quenching nucleotide and removal of that nucleotide allows for detection of the nucleic acid, extension of extension product to incorporate a detectable moiety is not necessary for the subsequent detection step.

Another alternative method for detection comprises incorporating a modified deoxynucleoside triphosphate (dNTP) into the extension product. Examples include radioactive, fluorescent and hapten labeled dNTPs. A fluorescent labeled dNTP, for example, allows direct nonradioactive detection. The sensitivity of this method, like the bioluminometric detection, is enhanced by utilizing an oligonucleotide which can hybridize to a region at or near the 5' end of the known template and that is capable of priming an extension reaction synthesis from a first nucleic acid. This method, like the Fluorogenic 5' Nuclease Assay, has the advantage of high sensitivity and specificity since the extension reaction can be performed at elevated temperatures, such as in a thermocycling reaction. This method can add an additional step to remove any unincorporated label, as described above, followed by direct or indirect detection of incorporated label. In one embodiment, solid-phase purification can be used to capture and purify the extended oligomers from any unincorporated fluorescent labeled dNTPs followed by fluorometric detection.

Yet another method of distinguishing those single-stranded extension products that had a 3'-terminal nucleotide that hybridized with the nucleotide at the corresponding position on the reference nucleic acid from those that had a 3'-terminal nucleotide that did not hybridize with the nucleotide at the corresponding position on the reference nucleic acid can comprise separating the products of the method for the presence of full-length extension products after the proofreading activity has replaced the 3'-terminal nucleotide and further extended the extension product by, for example, denaturing gel electrophoresis to visualize the single strands, both full-length and those that are not full-length.

In certain applications of the invention it may be desirable to amplify a mutation that compromises a small percentage of the total analyte, such as in early cancer detection where only a few malignant cells may be present in the total number of cells being analyzed. The selective amplification of mutant gene, where the mutation occurs at a known site, such as the K-ras gene, is readily accomplished by the design of specific primers to amplify the mutation as described by Stork et al. (*Oncogene*, 6:857–862 (1991)). However, selective amplification of a random mutation in a gene among a high percentage of wild type genes is not possible by standard PCR. In these applications, selective amplification of the mutant template may be preferred. Therefore, the extension products from the mutant template are purified from that known template and hybridized to purified amplified nucleic acid from the sample whose sequence is unknown. The amplified nucleic acid can be purified from residual primers prior to mixing with the extension products to prevent reamplification of the wild type template. The hybrid can, for example, be exposed to a thermostable polymerase and dNTPs under thermocycling conditions suitable for polymerization of the extension products. The extension products that were refractory to extension on the known template because of a 3' terminal mismatch, can now hybridize to the mutant template from which they were formed and are extended by the polymerase. Preferably, one of the dNTPs is labeled, for example, with a hapten such as digoxigenin, to allow solid phase capture of the extension products. Solid-phase capture of the hapten labeled extension products followed by standard PCR amplification, with the primers used for the initial target amplification, preferentially amplifies the template containing the mutation. The PCR product can then be sequenced by standard methods to specifically identify the precise position of the mutation or nucleotide variation.

Thus, in one embodiment, the invention provides a method of selectively amplifying a random nucleotide variation in a specific region of a nucleic acid molecule present in a sample of nucleic acid molecules comprising the region, wherein the sample comprises a mixture of nucleic acid molecules comprising the variation, and nucleic acid molecules that do not comprise the variation, said method comprising generating a first set of single-stranded extension products from the sample nucleic acid molecules in the presence of modified nucleotide bases and chain-terminating nucleotide bases, wherein the extension products incorporate modified nucleotides that limit exonuclease activity to the 3'-terminal nucleotide base, and wherein the extension products have variable lengths; hybridizing the variable length extension products to a reference nucleic acid that does not have the nucleotide variation; contacting the hybridizing nucleic acids with an enzyme which can remove and replace the 3'-terminal nucleotide of the extension products in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended; extending those extension products that can be further extended; separating these extension products from the reference nucleic acid; combining the separated extension products of step (e) with a second sample of nucleic acid molecules comprising the region, wherein the sample comprises a mixture of nucleic acid molecules comprising the variation, and nucleic acid molecules that do not comprise the variation; contacting these nucleic acids with a primer extension reaction mixture comprising labeled dNTPS, thus extending those extension products that could not be further extended in the previous extension step; separating the labeled extension products from the unlabeled extension products; and amplifying the labeled extension products.

Of course, as in the other methods disclosed herein, the enzyme which can remove and replace the 3'-terminal nucleotide base may be any of the "proofreading enzymes" described above, including a combination of enzymes, such as a first enzyme that removes the 3'-terminal nucleotide (e.g., an exonuclease), and a second enzyme which then replaces that 3'-terminal nucleotide (e.g., a polymerase). The hybridizing nucleic acids may either be contacted sequentially with the first enzyme followed by the second enzyme, or contacted simultaneously with the first enzyme and the second enzyme.

The present invention also provides a method of detecting nucleotide variation within a first nucleic acid, comprising generating a set of single-stranded extension products from the first nucleic acid in the presence of modified nucleotide bases, and optionally in the presence of chain-terminating nucleotide bases, wherein the extension products incorporate modified nucleotides that limit exonuclease activity to the 3'-terminal nucleotide base, and wherein the extension products have variable lengths, hybridizing the variable length extension products to a reference nucleic acid, contacting the hybridizing nucleic acids with an enzyme which can remove and replace the 3'-terminal nucleotide of the extension products in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended, extending those extension products that can be further extended, distinguishing those extension products that are further extended from those extension products that cannot be further extended, thereby detecting nucleotide variation in the first nucleic acid.

Figure 3:
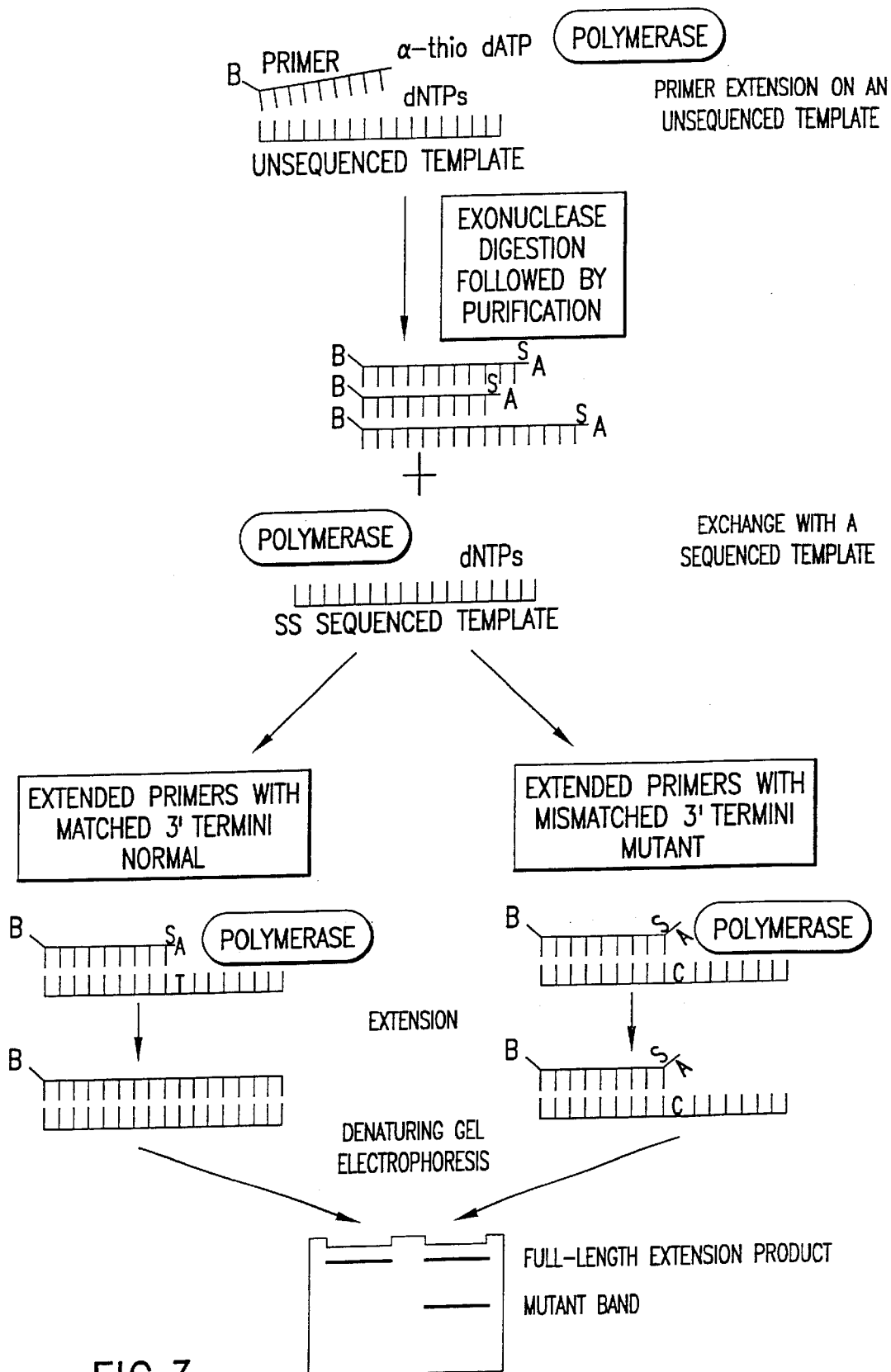
FIG. 3 shows a schematic for the non-extension template exchange extension reaction detection method using exo-resistant termini.
Figure 4:
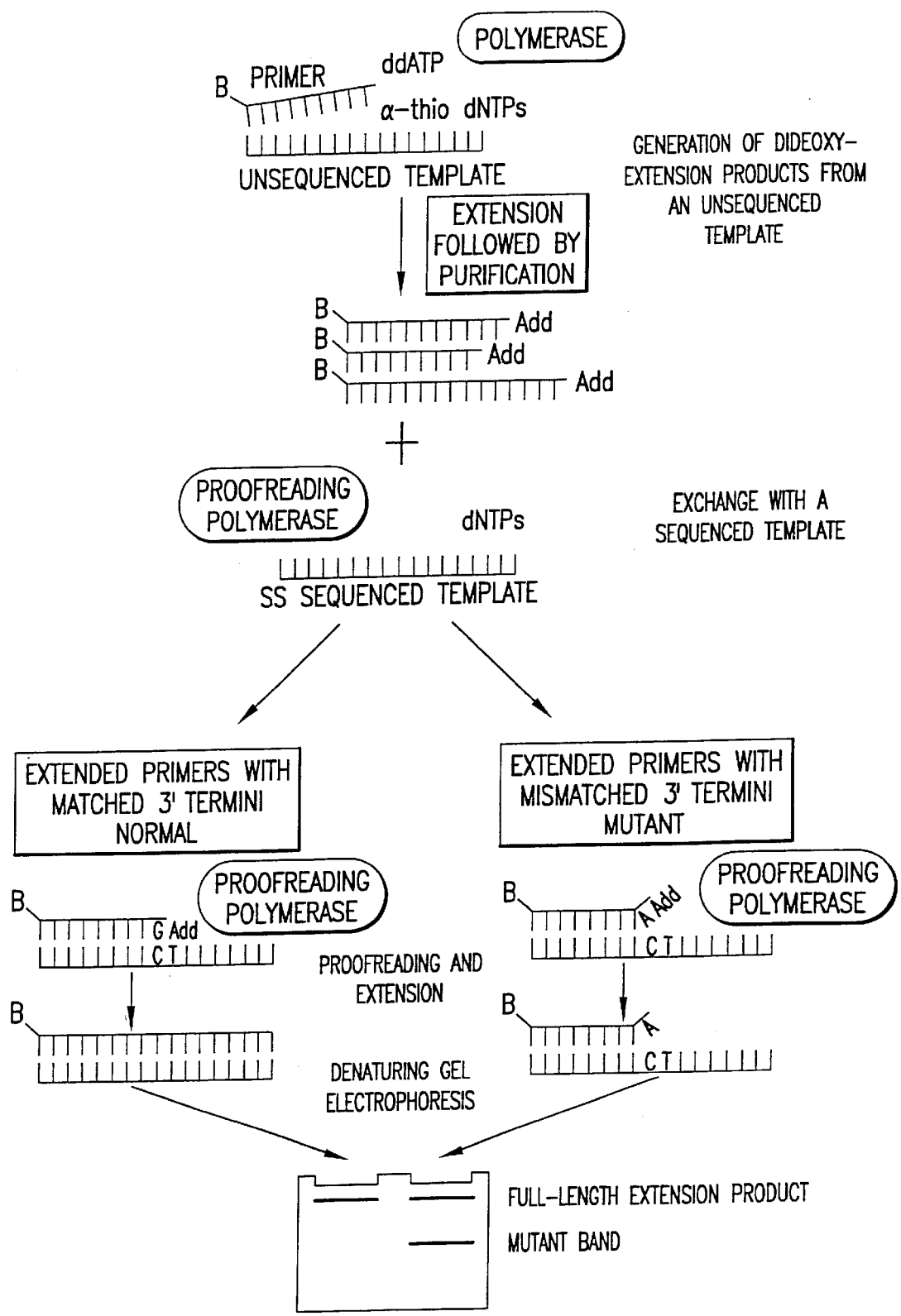
FIG. 4 shows a schematic for the non-extension template exchange extension reaction detection method using dideoxynucleotides incorporated at the 3'-termini.

This particular method is based on the inability of a proofreading polymerase to excise and or extend a mismatched 3' nucleotide that is resistant to removal by a 3'→5' exonuclease activity such as a thio-modified nucleotide or a borano-modified nucleotide. In this method, the set of single-stranded extension products of variable length are generated as described above, those extension products are hybridized to a reference nucleic acid, and the hybrid is contacted with a proofreading enzyme, or in an equivalent reaction as discussed above, in the presence of all four deoxynucleotides under conditions suitable for proofreading and polymerization. (FIGS. 3 and 4) In those single-stranded extension products where the 3'-terminal nucleotide matches the known reference nucleic acid, then the polymerase excises the chain-terminating nucleotide or other 3'-terminal nucleotide and replaces that nucleotide and further extends the extension product. However, if there is a mismatch at the modified nucleotide that is resistant to 3'→5' exonuclease activity adjacent (i.e. the 3'-terminal nucleotide (FIG. 3) or the penultimate 3' nucleotide (FIG. 4)) to a matched or mismatched 3'-terminal nucleotide, the proofreading enzyme will not excise that mismatched terminal or penultimate nucleotide and will be unable to further extend that extension product. The products of this reaction can then be analyzed, for example by denaturing gel electrophoresis, whereby the detection of non-further extended extension products indicates nucleotide variations between the unknown and the reference nucleic acid and further extension of the extension products indicates that the templates have base complementarity at their 3'-ends, and therefore no nucleotide variations are present at the 3'-end of the first nucleic acid relative to the reference nucleic acid.

Thus, in one embodiment, the invention provides a method of detecting nucleotide variation within a first nucleic acid, comprising generating a set of single-stranded extension products from the first nucleic acid in the presence of modified nucleotide bases and chain-terminating nucleotide bases, wherein the extension products incorporate modified nucleotides that limit exonuclease activity to the 3'-terminal nucleotide base, and wherein the extension products have variable lengths; hybridizing the variable length extension products to a reference nucleic acid; contacting the hybridizing nucleic acids with a first enzyme which can remove the 3'-terminal nucleotide of the extension products, and with a second enzyme which extends those extension products that can be further extended in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended; and distinguishing those extension products that are further extended from those extension products that cannot be further extended, thereby detecting nucleotide variation in the first nucleic acid. The hybridizing nucleic acids may either be contacted sequentially with the first enzyme followed by the second enzyme, or contacted simultaneously with the first enzyme and the second enzyme.

Since the identity of the terminal base is not critical to the embodiment that utilizes a chain-terminating nucleotide, that terminal base may be removed prior to hybridizing the single-stranded extension product with the reference nucleic acid. Several exonucleases with 3'→5' activity are suitable for this embodiment and are readily available. Some examples are exonuclease I and exonuclease III. Additionally, the removal of the terminal base obviates the need for a proofreading enzyme in the subsequent reaction. Therefore, enzymes which lack the 3' to 5' exonuclease activity, such as the large fragment of Bst DNA Polymerase and Taq DNA Polymerase, may be used for extension detection.

Also, since the 3'-terminal nucleotide needs only to be a suitable substrate for the extension activities of a polymerase, alternative sequencing methods can be used to generate the set of single-stranded extension products for use in this detection method. Examples include sequencing methods that use thiophosphate or boranophosphate modified nucleotide as delimiters in a primer extension reaction followed by enzymatic digestion with exonuclease III. (See Labeit et al., *DNA,* 5:173 (1986) and Porter, *Nucleic Acids Research* 25:1611–1617 (1997)). The series of single-stranded extension products of variable length generated by these processes can be terminated with a thio- or borano-modified nucleotide and are thus well suited for this method.

Other detection methods that may be used in the methods of the invention are described below.

A labeled dideoxynucleotide may also be rapidly detected by using MALDI-TOF Mass Spectrophotometry.

In another alternative method of the invention, the primer used for generating the extension products is labeled with a ruthenium metal complex (ORI-TAG labels from IGEN International) instead of biotin. A biotin labeled dideoxy nucleotide is then incorporated into the extension products in the final step. These extension products are then captured with magnetic beads coated with streptavidin, and the presence of the ruthenium label is detected. IGEN sells a machine to perform the capture and detection of the ruthenium label automatically.

Alternatively, the primer used for generating the extension products is unlabeled, and a biotin labeled dideoxy nucleotide is used in the final step. A ruthenium labeled probe is then hybridized to the extension products, and this duplex is then captured with magnetic beads coated with streptavidin. The ruthenium label may then be detected as described above.

The methods of the invention may also be performed in multiplex attaching templates to a specific fluorescent microsphere, thus associating each template with a unique fluorescent signal, such as Fluorescent Microspheres from Luminex. In this manner, an unknown sample may be simultaneously screened against a number of templates in one reaction vessel. This would be extremely useful when a particular gene has multiple alleles. In methods of the invention where incorporation of a labeled dideoxt nucleotide is desired (see, e.g., FIG. 1), fluorescently labeled dideoxy nucleotides may be used in a solid-phase extension reaction.

Figure 5:
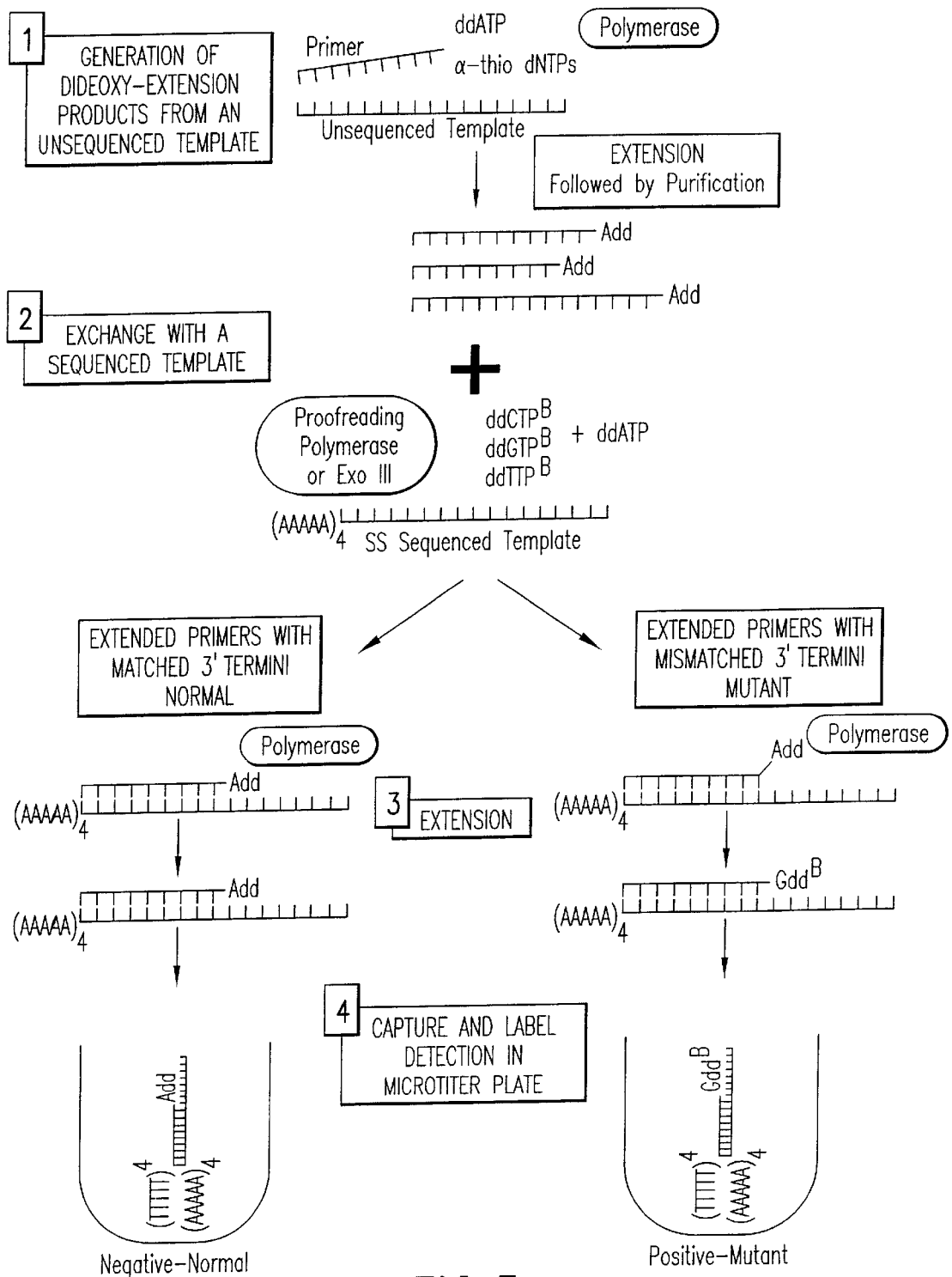
FIG. 5 is a diagram of an example of the methods of the invention adapted to a microtiter plate format.

Of course, the methods of the invention may readily be adapted to a microtiter plate format using methodology that is well known in the art. One example of such an adaptation is shown in FIG. 5. In this method, the dideoxy terminated sequencing products from the unsequenced template are mixed with a seqeunced template containing a poly-A capture tail (step 2). A proofreading enzyme or an exonuclease is used to selectively remove the terminal dideoxy nucleotide. The extension products are then extended in the presence of three labeled dideoxy nucleotides and one unlabeled dideoxy nucleotide that matches the former terminal dideoxy nucleotide (step 3). If the terminal dideoxy nucleotide matches the sequenced template, an unlabeled dideoxy will be inserted. If the terminal dideoxy nucleotide does not match the sequenced template, a labeled dideoxy will be inserted. This product is then captured in a microtiter well coated with a poly T oligonucleotide (Xenopore, Hawthorned, N.J.) The presence of the label is then detected. Preferable, the label is biotin (NEN, Boston, Mass.), and the biotin label is detected with a streptavidin alkaline phosphatase conjugate followed by luminescent detection in a microplate luminometer.

If greater sensitivity is needed, an alternative to this detection method is to use an anti-digoxigen aequorin conjugate (Sealite Sciences, Norcross, Ga.). In this method, a biotin label is used instead of the poly-A tail for capture. Digoxigenin labeled dideoxy nucleotides (NEN, Boston, Mass.) can be substituted for the biotin labeled nucleotides described above, and the extension products captired on a streptavidin coated microtiter plate (Xenopore). This technique has sensitivities in the 25 attomole range.Nov. 20, 2000

After it has been determined by any of the methods outlined above that a certain nucleic acid comprises a nucleotide variation as compared to the reference nucleic acid, it is possible to specifically identify the nucleotide variation by determining the sequence of the first nucleic acid which has been identified as having a sequence variation, and comparing that sequence to the sequence of the reference nucleic acid, thereby specifically identifying the nucleotide variation in the first nucleic acid. The sequence may be determined using any of the standard methods known in the art. Furthermore, as the first step of the above methods generate variable length extension products, it is possible to determine the sequence of the complement of the first nucleic acid by running the variable length extension products on a sequencing gel (i.e., polyacrylamide gel) to generate a sequencing ladder. Of course, in order to do this, a detectable label must be incorporated into the extension products in the initial extension reaction.

Where the method used to determine the presence of a variation in sequence results in the production of a primer that is not fully extended due to a nucleotide variation, as is the case in many of the methods described above, and in FIGS. 1, 3, and 4, that primer may also be run on the sequencing gel in order to further confirm the position of the sequence variation.

The following example is put forth so as to provide those of ordinary skill in the art with a complete disclosure and description of the claimed methods, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLES

Preparation of Template Molecules

Amplification of K-ras

A 275 base pair region of the K-ras gene exon 1 was amplified by the polymerase chain reaction (PCR) with the primer K-ras p-A (p-CAGAGAAACCTTTATCTG) (SEQ ID NO: 1) containing a 5' phosphate and K-ras B (GTACTGGTGGAGTATTT) (SEQ ID NO:2) as disclosed by Stork et al., *Oncogene*, 6:857–862 (1991). All primers were synthesized by Oligos Etc., Inc., Wilsonville, Oreg. The reaction (20 µl) contained 10 mM Tris-HCl, pH 8.3, 50 mM KCl, 2.0 mM $MgCl_2$, 1 pm/µl Kras A&B primer, 200 µM of each dNTP 1 ng/µl of K562 genomic DNA (Promega, Madison, Wis.) and 0.025 units/µl of Taq DNA polymerase (Perkin Elmer, Foster City, Calif.). Just prior to use the Taq polymerase was mixed with Taq Start antibody (Clontech, Palo Alto, Calif.) according to the manufacturer's directions. Thermocycling was done in a GeneAmp 9600 PCR System (Perkin Elmer) with the following program: Hold: 95° C. for 5 min, Cycle: 95° C. for 15 sec, 53° C. for 30 sec, 72° C. for 15 sec for 33 cycles, Hold: 72° C. for 5 min.

Sequence Determination

The amplified DNA was purified for cycle sequencing using the Wizard PCR Preps DNA Purification System (Promega). It was sequenced in both directions by using either the K-ras A or K-ras-B primer. Cycle sequencing and detection was done with the Silver Sequence DNA Sequencing System (Promega) as described by the manufacturer. The cycling conditions were: 95° C. for 5 min, Cycle: 95° C. for 30 sec, 50° C. for 30 sec, 72° C. for 60 sec for 60 cycles, Hold: 4° C. forever. The sequence was confirmed to be the wild type or normal sequence of cellular c-Ki-ras2 proto-oncogene exon 1 by BLAST analysis (Altschul et al., *J. Mol. Biol.*, 215:403–10 (1990)) against GenBank+EMBL+DDBJ+PDB databases at http://www.ncbi.nlm.nih.gov/BLAST.

Generation of Single-stranded Template

The purified PCR product was made single stranded by digestion with lambda exonuclease (Higuchi and Ochman, *Nucleic Acids Research*, 17:5865 (1989)) using the PCR Template Preparation Kit from Pharmacia Biotech, Inc., Piscataway, N.J.

Generation of Dideoxy-terminated Oligomers
Amplification and Sequencing

The same region of the k-ras gene was amplified from genomic DNA from the cell line SW480 (American Type Culture Collection, Rockville, Md.) and purified as outlined above. The purified template (40 ng) was mixed with 10 pm of K-ras b-A primer in 10 µl of 0.7×Sequenase Reaction Buffer (Amersham), heated to 100° C. for 2 min and then immediately cooled in an ice water bath for 5 min. Five µl of Enzyme Mix [1 µl of 0.1 M DTT (Amersham)+2 µl of 5×Sequenase Buffer (Amersham) +2 µl of Sequenase Version 2.0 (Amersham) diluted 1:8 in Enzyme Dilution Buffer (Amersham)] was added to the ice-cold DNA mixture. This mixture (3.5 µl) was then added to a tube at 37° C. containing 2.5 µl of 200 µM of each alpha-thio-dNTP (Amersham) 1 µM ddATP (Pharmacia). Similarly, this was repeated for each of the remaining three ddNTPs. After incubating the samples at 37° C. for 5 min, 30 µl of 1×TE pH 7.5 (10 mM Tris-Cl pH 7.5 1 mM EDTA) was added to each tube to stop the reaction.

Purification of Extension Products from Template

Streptavidin-coated magnetic beads (Dynabeads M-280, Dynal Inc., Lake Success, N.Y.) were used for solid-phase capture of extension products. Prior to use, Dynabeads were washed in 2×B&W buffer (10 mM Tris-HCl, pH 7.5, 1 mM EDTA, 2 M NaCl) according the manufacturer's directions. For each completed dideoxy sequencing reaction, 40 µl of 1.25 µg/µl streptavidin-coated magnetic beads in 2×B&W buffer was added to each reaction. After incubating for 15 minutes at room temperature with intermittent vortexing the beads were captured and washed with 40 µl of 2×B&W buffer. Melting of the DNA duplex and strand separation were performed according to the manufacturer's directions.

Generation of Alpha-thio Terminated Oligomers from a Mutant and Wild Type Template The same region of the k-ras gene was amplified from genomic DNA from the both the K562 and SW480 (American Type Culture Collection, Rockville, Md.) cell line and purified as outlined above. The purified template (240 ng) was mixed with 60 pm of K-ras b-A primer in 60 µl of 0.07×Sequenase Reaction Buffer, dispensed in three 20 µl aliquots, heated to 100° C. for 3 min and then immediately cooled in an ice water bath for 5 min. Ten µl of Enzyme Mix (1 µl of 0.1 M DTT+2 µl of 5×Sequenase Buffer+2 µl of Sequenase Version 2.0 diluted 1:8 in Enzyme Dilution Buffer) was added to the ice-cold DNA mixture. This mixture (28 µl) was then added to a tube at 37° C. containing 20 µl of 26 µM alpha-thio-dATP 54 µM dATP 80 µM of the remaining three dNTPs. After incubating the samples at 37° C. for 5 min the reaction was inactivated by heating at 75° C. for 10 minutes. Sixteen µl of a solution containing 20 U/µl Exonuclease III (Promega) in 7×Exonuclease III Buffer (Promega) was added to each inactivated extension reaction. The reactions were incubated at 37° C. for 30 minutes and then heat inactivated at 70° C. for 10 minutes.

Extension Detection of Nucleotide Variations
Non-extension Detection

Two hybridization reactions were set up for SW480 and K562 alpha-thio terminated oligomers, one containing ss k-ras template DNA from K562 and one without template DNA. The template containing hybridization reaction contained the following: 36 µl of alpha-thio terminated oligomers from either K562 or SW480, 100 ng of ss k-ras template from K562, 60 µl of 2×B&W buffer (10 mM Tris-HCl, pH 7.5, 1.0 mM EDTA, 2 M NaCl) and molecular biology grade (MBG) water (Sigma, W-4502, St. Louis, Mo.) to a final volume of 120 µl. A parallel reaction was setup without template DNA. The reactions were heated at 99.9° C. for 2 min and cooled 1° C./min to 58° C. The reaction was transferred to a Microcon YM-30 centrifugal filter device and spun 5 minutes at 7200×g. The retentate was mixed with 450 µl of MBG water and reconcentrated two times. The retentate was adjusted to a final volume of 12 µl with MBG water. Six µl of the retenatete was mixed with 4 µl extension master mix: 25 mM Tris-HCl, pH 8.3, 125 mM KCl, 5.0 mM MgCl$_2$, 500 µM of each dNTP and 0.125 units/µl of Taq DNA polymerase (Perkin Elmer). Just prior to use the Taq polymerase was mixed with Taq Start antibody (Clontech, Palo Alto, Calif.) according to the manufacturer's directions. The reactions were thermocycled as follows: Hold: 95° C. for 5 min, Cycle: 95° C. for 15 sec then 94° C. for 15 sec with a 2° C. decrease/cycle for 14 cycles, Cycle: 95° C. for 15 sec, 68° C. for 15 sec with a 2° C. decrease/cycle, 72° C. for 15 sec for 19 cycles. Upon completion, 4 µl of stop solution (95% formamide, 20 mM EDTA, 0.05% bromophenol blue, 0.05% xylene cyanol FF) was added to each reaction. Three µl of the supernatant was loaded on a 0.4 mm×20 cm×34 cm 6% denaturing polyacrylamide gel for analysis. The gel was preheated at 40 W for 30 minutes before loading the samples and running at 40 w for 50 min. The Phototope-Star Detection Kit (New England Biolabs) was used for chemiluminescent detection of the biotinylated extension products as described by the manufacturer.

Single Base Extension Detection

Six µl of single-base extension master mix containing: 1×ThermoPol Reaction Buffer (New England Biolabs, Inc., Beverly, Mass.) 2.0 mM MgSO$_4$, 200 µM of an unlabeled ddNTP that matches the terminal dideoxynucleotide, 200 µM of the 3 remaining ddNTPs labeled with $^{33}$P (Amersham), 1 ng/µl of single-stranded template DNA and 0.01 units/µl of Vent DNA polymerase (New England Biolabs, Inc.) was used to suspend the solid-phase extension products. Thermocycling was as follows: Hold: 95° C. for 5 min, Cycle: 95° C. for 15 sec then 94° C. for 15 sec with a 2° C. decrease/cycle for 14 cycles, Cycle: 95° C. for 15 sec, 68° C. for 15 sec with a 2° C. decrease/cycle, 72° C. for 15 sec for 19 cycles, Hold: 4° C.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of detecting a nucleotide variation within a first nucleic acid, comprising:
   a) generating a set of single-stranded extension products from the first nucleic acid in the presence of modified nucleotide bases, wherein the extension products incorporate modified nucleotides and thereby limit exonuclease activity to the 3'-terminal nucleotide base, and wherein the extension products have variable lengths;
   b) hybridizing the variable length extension products to a reference nucleic acid;
   c) contacting the hybridizing nucleic acids with a first enzyme which can remove the 3'-terminal nucleotide of the extension products, and with a second enzyme which extends those extension products that can be further extended in the presence of selected labeled nucleotides, wherein extension products that terminate with a 3'-nucleotide that does not hybridize with the corresponding position on the reference nucleic acid are replaced with a nucleotide that hybridizes with the corresponding nucleotide on the reference nucleic acid and wherein those extension products that had a non-hybridizing nucleotide at the 3'-terminus can now be distinguished from those extension products that had a hybridizing nucleotide at the 3'-terminus; and
   d) distinguishing those extension products that had a non-hybridizing nucleotide at their 3'-terminus from those extension products that had a hybridizing nucleotide at their 3'-terminus, thereby detecting nucleotide variation in the first nucleic acid.

2. The method of claim 1, wherein the modified nucleotides comprise thio-modified deoxynucleotides.

3. The method of claim 1, wherein the modified nucleotides comprise borano-modified deoxynucleotides.

4. The method of claim 1, wherein the first enzyme of step (c) is a 3' to 5' exonuclease, and the second enzyme of step (c) is a DNA polymerase.

5. The method of claim 1, wherein in step (c), the hybridizing nucleic acids are contacted sequentially with the first enzyme followed by the second enzyme.

6. The method of claim 1, wherein in step (c), the hybridizing nucleic acids are contacted simultaneously with the first enzyme and the second enzyme.

7. The method of claim 1, wherein the extension products are modified.

8. The method of claim 7, wherein the modification comprises linking biotin to the extension product.

9. The method of claim 7, wherein the modification comprises linking a hapten to the extension product.

10. The method of claim 7, further comprising isolating the extension products of step (a) by binding them to a solid support.

11. The method of claim 8, wherein the extension products are labeled with biotin and are isolated by binding them to a solid support coated with streptavidin.

12. The method of claim 1, wherein step (c) further comprises performing the contacting step in the presence of the selected nucleotide base in the form of a second label-labeled dideoxynucleoside triphosphate, thereby providing a positive control for functioning of the enzyme.

13. The method of claim 1, wherein the extension products are variable length by incorporation of chain-terminating nucleotides into the extension products.

14. The method of claim 1, wherein the extension products are variable length by partial exonuclease digestion of the extension products.

15. The method of claim 1, comprising the additional step of determining the sequence of the first nucleic acid which has been identified as having a sequence variation and comparing that sequence to the sequence of the reference nucleic acid, thereby specifically identifying the nucleotide variation in the first nucleic acid.

16. A method of detecting a nucleotide variation within a first nucleic acid and specifically identifying the nucleotide variation, comprising:
   a) generating a set of single-stranded extension products from the first nucleic acid in the presence of modified nucleotide bases, wherein the extension products incorporate modified nucleotides and thereby limit exonuclease activity to the 3'-terminal nucleotide base, and wherein the extension products have variable lengths;

b) hybridizing the variable length extension products to a reference nucleic acid;

c) contacting the hybridizing nucleic acids with an enzyme which can remove and replace the 3'-terminal nucleotide of the extension products in the presence of selected labeled nucleotides, wherein extension products that terminate with a 3'-nucleotide that does not hybridize with the corresponding position on the reference nucleic acid are replaced with a nucleotide that hybridizes with the corresponding nucleotide on the reference nucleic acid and wherein those extension products that had a non-hybridizing nucleotide at the 3'-terminus can now be distinguished from those extension products that had a hybridizing nucleotide at the 3'-terminus;

d) distinguishing those extension products that had a non-hybridizing nucleotide at their 3'-terminus from those extension products that had a hybridizing nucleotide at their 3'-terminus, thereby detecting nucleotide variation in the first nucleic acid; and e) determining the sequence of the first nucleic acid which has been identified as having a sequence variation and comparing that sequence to the sequence of the reference nucleic acid, thereby specifically identifying the nucleotide variation.

17. A method of detecting within a first nucleic acid the presence of a nucleotide, comprising:

a) generating a set of single-stranded extension products from the first nucleic acid in the presence of modified nucleotide bases, wherein the extension products incorporate modified nucleotides that limit exonuclease activity to the 3'-terminal nucleotide base, and wherein the extension products have variable lengths;

b) hybridizing the variable length extension products to a reference nucleic acid;

c) contacting the hybridizing nucleic acids with a first enzyme which can remove the 3'-terminal nucleotide of the extension products, and with a second enzyme which extends those extension products that can be further extended in the presence of a selected modified nucleotide which is resistant to further replacement and when incorporated into an extension product inhibits further extension of the extension product, wherein extension products that terminate with a non-modified nucleotide can be further extended and thereby distinguished from those extension products that cannot be further extended;

d) removing the unincorporated selected modified nucleotide;

e) extending those extension products that can be further extended; and f) distinguishing those extension products that are further extended from those extension products that cannot be further extended, thereby detecting nucleotide variation in the first nucleic acid.

18. The method of claim 17, wherein the selected modified nucleotide comprises a thio-modified dideoxynucleotide triphosphate.

19. The method of claim 17, wherein the selected modified nucleotide comprises a borano-modified dideoxynucleotide triphosphate.

20. The method of claim 17, wherein step (d) further comprises adding the enzyme shrimp alkaline phosphatase under conditions suitable for activity of the enzyme followed by inactivating the enzyme.

21. The method of claim 17, wherein in step (c), the hybridizing nucleic acids are contacted sequentially with the first enzyme followed by the second enzyme.

22. The method of claim 17, wherein in step (c), the hybridizing nucleic acids are contacted simultaneously with the first enzyme and the second enzyme.

23. The method of claim 17, wherein the extension products are modified.

24. The method of claim 23, wherein the modification comprises linking biotin to the extension product.

25. The method of claim 23, wherein the modification comprises linking a hapten to the extension product.

26. The method of claim 17, further comprising isolating the extension products of step (a) by binding them to a solid support.

27. The method of claim 24, wherein the extension products are labeled with biotin and are isolated by binding them to a solid support coated with streptavidin.

28. The method of claim 17, wherein the extension products are variable length by incorporation of chain-terminating nucleotides into the extension products.

29. The method of claim 17, wherein the extension products are variable length by partial exonuclease digestion of the extension products.

30. The method of claim 17, comprising the additional step of determining the sequence of the first nucleic acid which has been identified as having a sequence variation and comparing that sequence to the sequence of the reference nucleic acid, thereby specifically identifying the nucleotide variation in the first nucleic acid.

31. A method of detecting within a first nucleic acid the presence of a nucleotide variation and specifically identifying the nucleotide variation, comprising:

a) generating a set of single-stranded extension products from the first nucleic acid in the presence of modified nucleotide bases, wherein the extension products incorporate modified nucleotides that limit exonuclease activity to the 3'-terminal nucleotide base, and wherein the extension products have variable lengths;

b) hybridizing the variable length extension products to a reference nucleic acid;

c) contacting the hybridizing nucleic acids with an enzyme which can remove and replace the 3'-terminal nucleotide of the extension products in the presence of a selected modified nucleotide which is resistant to further replacement and when incorporated into an extension product inhibits further extension of the extension product, wherein extension products that terminate with a non-modified nucleotide can be further extended and thereby distinguished from those extension products that cannot be further extended;

d) removing the unincorporated selected modified nucleotide;

e) extending those extension products that can be further extended;

f) distinguishing those extension products that are further extended from those extension products that cannot be further extended, thereby detecting nucleotide variation in the first nucleic acid; and g) determining the sequence of the first nucleic acid which has been identified as having a sequence variation and comparing that sequence to the sequence of the reference nucleic acid, thereby specifically identifying the nucleotide variation.

32. A method of detecting nucleotide variation within a first nucleic acid, comprising:
  a) generating a set of single-stranded extension products from the first nucleic acid in the presence of modified nucleotide bases and chain-terminating nucleotide bases, wherein the extension products incorporate modified nucleotides that limit exonuclease activity to the 3'-terminal nucleotide base, and wherein the extension products have variable lengths;
  b) hybridizing the variable length extension products to a reference nucleic acid;
  c) contacting the hybridizing nucleic acids with a first enzyme which can remove the 3'-terminal nucleotide of the extension products, and with a second enzyme which extends those extension products that can be further extended in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended; and
  d) distinguishing those extension products that are further extended from those extension products that cannot be further extended, thereby detecting nucleotide variation in the first nucleic acid.

33. The method of claim 32, wherein in step (c), the hybridizing nucleic acids are contacted sequentially with the first enzyme followed by the second enzyme.

34. The method of claim 32, wherein in step (c), the hybridizing nucleic acids are contacted simultaneously with the first enzyme and the second enzyme.

35. The method of claim 32, wherein the single stranded extension products are labeled with a detectable label and the distinguishing step (d) comprises performing gel electrophoresis of the reaction from step (c), wherein the electrophoresis is of sufficient resolution to distinguish between a labeled extension product that is not further extended and a labeled extension product that is further extended.

36. The method of claim 32, wherein the modified nucleotides comprise thio-modified deoxynucleotides.

37. The method of claim 32, wherein the modified nucleotides comprise borano-modified deoxynucleotides.

38. The method of claim 32, wherein the extension products are modified.

39. The method of claim 38, wherein the modification comprises linking biotin to the extension product.

40. The method of claim 39, wherein the modification comprises linking a hapten to the extension product.

41. The method of claim 32, further comprising isolating the extension products of step (a) by binding them to a solid support.

42. The method of claim 39, wherein the extension products are labeled with biotin and are isolated by binding them to a solid support coated with streptavidin.

43. The method of claim 32, comprising the additional step of determining the sequence of the first nucleic acid which has been identified as having a sequence variation and comparing that sequence to the sequence of the reference nucleic acid, thereby specifically identifying the nucleotide variation in the first nucleic acid.

44. A method of detecting nucleotide variation within a first nucleic acid, and specifically identifying the nucleotide variation, comprising:
  a) generating a set of single-stranded extension products from the first nucleic acid in the presence of modified nucleotide bases and chain-terminating nucleotide bases, wherein the extension products incorporate modified nucleotides that limit exonuclease activity to the 3'-terminal nucleotide base, and wherein the extension products have variable lengths;
  b) hybridizing the variable length extension products to a reference nucleic acid;
  c) contacting the hybridizing nucleic acids with an enzyme which can remove and replace the 3'-terminal nucleotide of the extension products in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended;
  d) extending those extension products that can be further extended;
  e) distinguishing those extension products that are further extended from those extension products that cannot be further extended, thereby detecting nucleotide variation in the first nucleic acid; and
  f) determining the sequence of the first nucleic acid which has been identified as having a sequence variation and comparing that sequence to the sequence of the reference nucleic acid, thereby specifically identifying the nucleotide variation.

45. A method of detecting within a first nucleic acid the presence of a nucleotide variation and specifically identifying the nucleotide variation, comprising:
  a) generating a set of single-stranded extension products from the first nucleic acid in the presence of modified nucleotide bases, wherein the extension products incorporate modified nucleotides that inhibit exonuclease activity at the 3'-terminal nucleotide base, and wherein the extension products have variable lengths;
  b) hybridizing the variable length extension products to a reference nucleic acid;
  c) contacting the hybridizing nucleic acids with an enzyme which, in the presence of deoxynucleotide triphosphates, can further extend those extension products that have a 3'-terminal nucleotide that hybridizes with the corresponding position on the reference nucleic acid and whereby extension products containing a 3'-terminal nucleotide that does not hybridize with the corresponding position on the reference nucleic acid are not further extended, and wherein an extension product that cannot be further extended is generated from a first nucleic acid that comprises a nucleotide variation;
  d) extending those extension products that can be further extended;
  e) distinguishing those extension products that are further extended from those extension products that cannot be further extended, thereby detecting nucleotide variation in the first nucleic acid; and
  f) determining the sequence of the first nucleic acid which has been identified as having a sequence variation and comparing that sequence to the sequence of the reference nucleic acid, thereby specifically identifying the nucleotide variation.

46. The method of claim 45, wherein the extension products are variable length by partial exonuclease digestion of the extension products.

47. A method of selectively amplifying a random nucleotide variation in a specific region of a nucleic acid molecule present in a sample of nucleic acid molecules comprising the region, wherein the sample comprises a mixture of nucleic acid molecules comprising the variation, and nucleic acid molecules that do not comprise the variation, said method comprising:

a) generating a first set of single-stranded extension products from the sample nucleic acid molecules in the presence of modified nucleotide bases and chain-terminating nucleotide bases, wherein the extension products incorporate modified nucleotides that limit exonuclease activity to the 3'-terminal nucleotide base, and wherein the extension products have variable lengths;
   b) hybridizing the variable length extension products of step (a) to a reference nucleic acid that does not have the nucleotide variation;
   c) contacting the hybridizing nucleic acids with a first enzyme which can remove the 3'-terminal nucleotide of the extension products, and with a second enzyme which extends those extension products that can be further extended in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended;
   d) separating the extension products of step (d) from the reference nucleic acid;
   e) combining the separated extension products of step (e) with a second sample of nucleic acid molecules comprising the region, wherein the sample comprises a mixture of nucleic acid molecules comprising the variation, and nucleic acid molecules that do not comprise the variation;
   f) contacting the nucleic acids of step (f) with a primer extension reaction mixture comprising labeled dNTPS, thus extending those extension products that could not be further extended in step (d);
   (g) separating the labeled extension products from the unlabeled extension products; and
   (h) amplifying the labeled extension products.

48. The method of claim 47, wherein in step (c), the hybridizing nucleic acids are contacted sequentially with the first enzyme followed by the second enzyme.

49. The method of claim 47, wherein in step (c), the hybridizing nucleic acids are contacted simultaneously with the first enzyme and the second enzyme.

50. The method of claim 47, further comprising sequencing the labeled extension products of step (i), and comparing that sequence to the sequence of the reference nucleic acid, thus specifically identify the nucleotide variation.

51. A method of selectively amplifying a random nucleotide variation in a specific region of a nucleic acid molecule present in a sample of nucleic acid molecules comprising the region, wherein the sample comprises a mixture of nucleic acid molecules comprising the variation, and nucleic acid molecules that do not comprise the variation, said method comprising:

a) generating a first set of single-stranded extension products from the sample nucleic acid molecules in the presence of modified nucleotide bases and chain-terminating nucleotide bases, wherein the extension products incorporate modified nucleotides that limit exonuclease activity to the 3'-terminal nucleotide base, and wherein the extension products have variable lengths;
   b) hybridizing the variable length extension products of step (a) to a reference nucleic acid that does not have the nucleotide variation;
   c) contacting the hybridizing nucleic acids with an enzyme which can remove and replace the 3'-terminal nucleotide of the extension products in the presence of deoxynucleotide triphosphates, wherein the penultimate 3'-nucleotide is resistant to removal from the extension products, whereby extension products containing a penultimate 3'-nucleotide that does not hybridize with the corresponding position on the reference nucleic acid is not replaced with a nucleotide that hybridizes with the corresponding nucleotide on the reference nucleic acid and thereby cannot be further extended;
   d) extending those extension products that can be further extended;
   e) separating the extension products of step (d) from the reference nucleic acid;
   f) combining the separated extension products of step (e) with a second sample of nucleic acid molecules comprising the region, wherein the sample comprises a mixture of nucleic acid molecules comprising the variation, and nucleic acid molecules that do not comprise the variation;
   g) contacting the nucleic acids of step (f) with a primer extension reaction mixture comprising labeled dNTPS, thus extending those extension products that could not be further extended in step (d);
   (h) separating the labeled extension products from the unlabeled extension products; and
   (i) amplifying the labeled extension products.

52. The method of claim 51, further comprising sequencing the labeled extension products of step (i), and comparing that sequence to the sequence of the reference nucleic acid, thus specifically identify the nucleotide variation.

* * * * *